(12) United States Patent
Afanasewicz et al.

(10) Patent No.: US 9,131,900 B2
(45) Date of Patent: Sep. 15, 2015

(54) FORCE REGULATING DEVICE APPLICATORS

(75) Inventors: Elizabeth A. Afanasewicz, Chestnut Hill, MA (US); Robert P. Harhen, Haverhill, MA (US); Adam J. Young, Dedham, MA (US); Rafael M. Cordero, Bedford, MA (US); Gerald Powers, Walpole, MA (US)

(73) Assignee: Covidien LP, Mansfield, MA (US)

( * ) Notice: Subject to any disclaimer, the term of this patent is extended or adjusted under 35 U.S.C. 154(b) by 423 days.

(21) Appl. No.: 13/546,142

(22) Filed: Jul. 11, 2012

(65) Prior Publication Data

US 2013/0023749 A1 Jan. 24, 2013

Related U.S. Application Data

(60) Provisional application No. 61/506,370, filed on Jul. 11, 2011.

(51) Int. Cl.
| | |
|---|---|
| *A61N 1/00* | (2006.01) |
| *A61B 5/00* | (2006.01) |
| *A61B 5/04* | (2006.01) |
| *A61B 17/34* | (2006.01) |
| *A61B 5/0478* | (2006.01) |
| *A61N 1/05* | (2006.01) |
| *A61N 1/04* | (2006.01) |
| *A61M 37/00* | (2006.01) |

(52) U.S. Cl.
CPC ............ *A61B 5/6885* (2013.01); *A61B 5/0478* (2013.01); *A61B 5/6814* (2013.01); *A61B 5/6832* (2013.01); *A61B 2562/0209* (2013.01); *A61B 2562/043* (2013.01); *A61M 2037/0023* (2013.01); *A61N 1/0452* (2013.01); *A61N 1/0456* (2013.01); *A61N 1/0472* (2013.01); *A61N 1/0502* (2013.01)

(58) Field of Classification Search
CPC .. A61B 5/0478; A61B 5/0492; A61B 5/0425; A61B 5/0532; A61B 5/4041; A61B 5/6848; A61B 5/6682; A61B 2019/464–2019/465; A61N 1/0502; A61N 1/0452
USPC ........... 600/386, 391–393, 397, 587, 372, 86; 606/186; 607/46–47, 153, 173
See application file for complete search history.

(56) References Cited

U.S. PATENT DOCUMENTS

| | | | |
|---|---|---|---|
| 3,356,369 A | 12/1967 | Stubbman | |
| 4,685,464 A | 8/1987 | Goldberger et al. | |
| 4,693,711 A * | 9/1987 | Bremer et al. | ................. 604/306 |
| 4,916,275 A | 4/1990 | Almond | |
| 5,135,262 A | 8/1992 | Smith et al. | |
| 5,224,478 A | 7/1993 | Sakai et al. | |
| 5,247,931 A | 9/1993 | Norwood | |
| 5,305,746 A | 4/1994 | Fendrock | |
| 5,309,909 A * | 5/1994 | Gadsby et al. | ................. 600/386 |
| 5,311,865 A | 5/1994 | Mayeux | |
| 5,377,675 A | 1/1995 | Ruskewicz et al. | |
| 5,813,980 A | 9/1998 | Levinson et al. | |
| 5,978,693 A | 11/1999 | Hamilton et al. | |

(Continued)

*Primary Examiner* — Joseph Stoklosa
*Assistant Examiner* — Brian M Antiskay
(74) *Attorney, Agent, or Firm* — Shvarts & Leiz LLP

(57) ABSTRACT

Disclosed herein are apparatus and techniques for applying a device to a subject. Such apparatus and techniques may provide feedback to an operator and/or regulate the force used to apply the device, yielding an improved result. Particularly useful embodiments include apparatus and techniques for applying a medical device, such as a skin surface electrode or microneedle array, to a patient's tissue.

22 Claims, 9 Drawing Sheets

(56) References Cited

U.S. PATENT DOCUMENTS

| | | |
|---|---|---|
| 6,785,569 B2 | 8/2004 | Schmidt et al. |
| 7,024,235 B2 | 4/2006 | Melker et al. |
| 7,127,278 B2 | 10/2006 | Melker et al. |
| 2002/0016537 A1 | 2/2002 | Muz et al. |
| 2004/0172115 A1* | 9/2004 | Miazga et al. ............... 607/116 |
| 2005/0137531 A1 | 6/2005 | Prausnitz et al. |
| 2006/0020179 A1 | 1/2006 | Anderson et al. |
| 2006/0064024 A1 | 3/2006 | Schnall |
| 2007/0073122 A1 | 3/2007 | Hoarau |
| 2007/0142717 A1 | 6/2007 | Lowery et al. |
| 2012/0179062 A1* | 7/2012 | Wilson .......................... 600/544 |
| 2013/0023748 A1 | 1/2013 | Afanasewicz et al. |

* cited by examiner

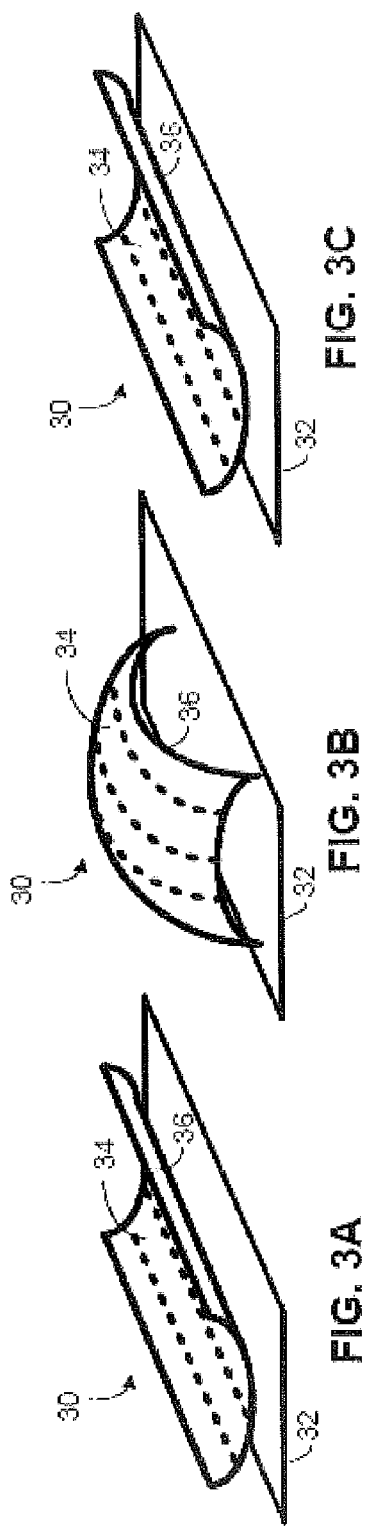
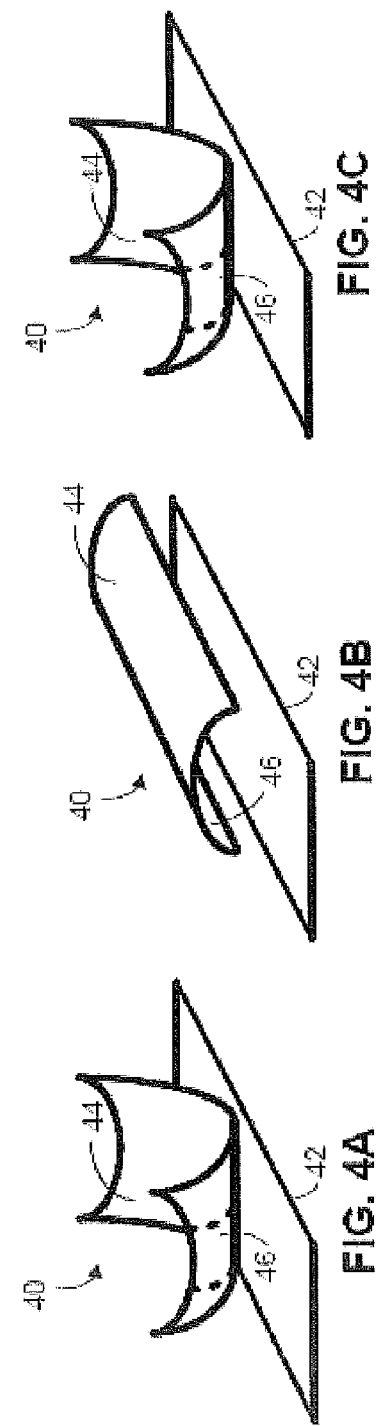

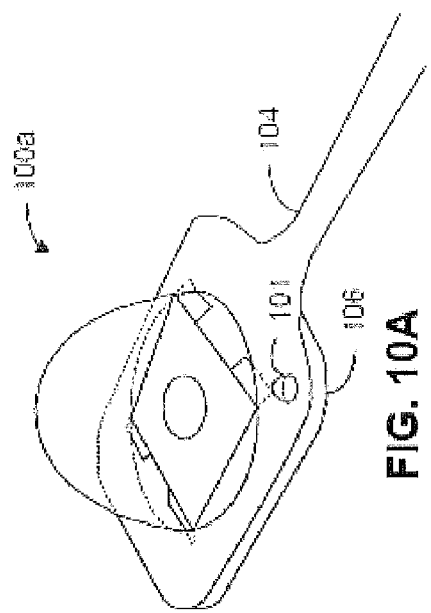
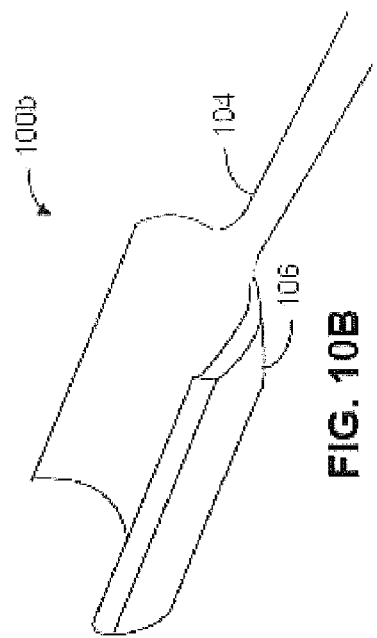
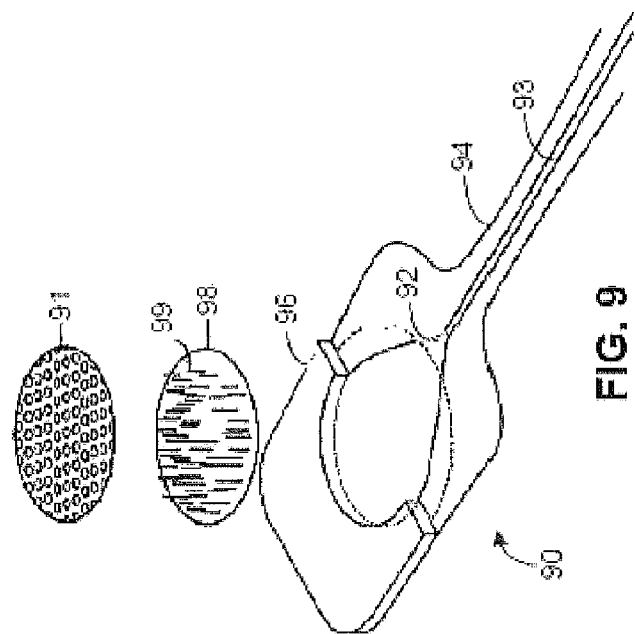

FORCE REGULATING DEVICE APPLICATORS

SUMMARY OF THE DISCLOSURE

Many procedures involve the application of a device to a surface. The device may be intended to mount, to attach, or to stay in contact with the surface, or may be intended for temporary or intermittent contact. In medical contexts, a monitoring or treatment device (such as a pre-gelled, self-prepping electrode) may be applied to a patient by pressing the device against the patient's tissue. In some procedures, it is important to apply the device to the surface with an appropriate amount, duration and direction of force to achieve successful application. For example, if a pre-gelled, self-prepping electrode is pressed against a patient's tissue with too much force, the conductive gel may be squeezed out from between the electrode and the patient tissue, reducing the electrical coupling between the electrode and the patient and thus the efficacy of a medical monitoring or treatment procedure. Alternately, if such a pre-gelled, self-prepping electrode is not applied with enough force, the self-prepping mechanism may fail to engage with the patient's tissue (e.g., fail to create conductive channels between the underlying layers of tissue and the electrode), also reducing the efficacy of the medical procedure. Moreover, the amount of force used to apply a device to a surface is likely to vary from application to application by a single operator, and will also vary between operators. Such variation may have detrimental effects on the reliability, consistency and quality of any procedure involving the device.

Described herein are apparatus and techniques for applying a device to a surface that address the challenges described above. These apparatus and techniques provide force regulation and feedback mechanisms to improve the quality of the contact between a device and an application surface, as well as to reduce the variability between applications, thereby improving consistency and reliability. Particular embodiments of these apparatus and techniques suitable for use in medical contexts are also provided.

BRIEF DESCRIPTION OF THE DRAWINGS

FIGS. 3A-3C depict an illustrative force regulator including a bistable spring in accordance with an embodiment;

FIGS. 4A-4C depict another illustrative force regulator including a bistable spring in accordance with an embodiment

FIG. 9 is an exploded perspective view of an illustrative medical device capable of being applied to a subject in accordance with the application techniques described herein;

FIGS. 10A-10B depict illustrative device applicators integrated with the medical device of FIG. 9, each in accordance with an embodiment;

DETAILED DESCRIPTION

Disclosed herein are apparatus and techniques for applying a device to a subject. As described above, such apparatus and techniques may provide feedback to an operator and/or regulate the force used to apply the device, yielding an improved result. Particularly useful embodiments include apparatus and techniques for applying a medical device, such as a skin surface electrode or microneedle array, to a patient's tissue.

Figure 1A:
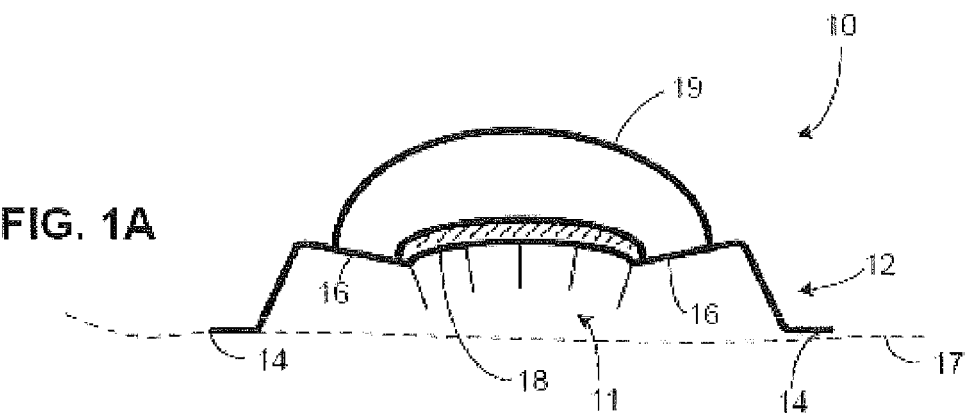
FIGS. 1A-1C depict an illustrative device applicator including a force regulator in accordance with an embodiment.
Figure 1B:
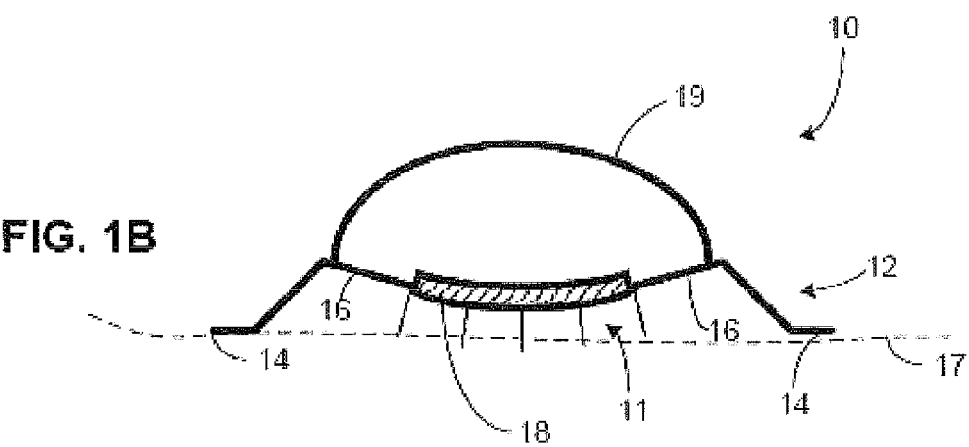
Figure 1C:
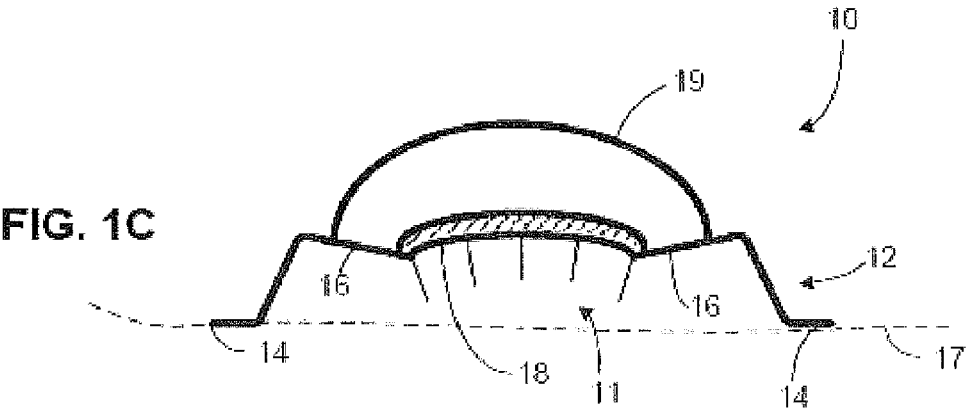

FIGS. 1A-1C depict illustrative device applicator 10 including force regulator 12, in accordance with an embodiment. Force regulator 12 may include supports 14, force directing members 16 and resilient member 18. Device applicator 10 may be configured to interface with device 11, which may have a contact portion. As depicted, the contact portion may include tines. Actuator 19 may also be included with device applicator 10.

Force regulator 12 may operate similarly to the cricket spring described in Stubbman, U.S. Pat. No. 3,356,369, entitled "DIE AGITATING CHANCE DEVICE," which is incorporated by reference in its entirety herein. Similar devices are well-known in the art, and may also be described as popper springs or snap springs. FIG. 1A depicts force regulator 12 in a first, relaxed configuration on surface 17. When a downward force is applied to force directing members 16, force regulator 12 may be deformed into a second, stressed configuration as shown in FIG. 1B. In particular, supports 14 may translate outwardly along surface 17 and force directing members 16 may bow downwardly toward surface 17. Once force directing members 16 have bowed to a predetermined extent, resilient member 18 may move from the upwardly arched position depicted in FIG. 1A to the downwardly arched position depicted in FIG. 1B. This movement to a downwardly arched position may be accompanied by a snapping or clicking sound, which may indicate to an operator that sufficient force has been applied. The downward force applied to force directing members 16 may be provided by an operator or mechanical device applying downward pressure to actuator 19, which may be a member capable of translating downward force to force directing members 16 (such as a rigid dome or plate). Actuator 19 may also include an elastomeric or cushioned material at the point of contact between an operator and device applicator 10. When the downward force is released, resilient member 18 rapidly moves back to its first configuration (FIG. 1C), and may produce a snapping or clicking sound. As discussed in additional detail below, the rapid movement of resilient member 18 may provide tactile feedback to an operator. The other elements of force regulator 12 may also return to their relaxed configurations once the downward force is released, as depicted in FIG. 1C.

In different embodiments, the tines illustrated in the contact portion of device applicator 10 may include any of a number of different types of contact members designed for piercing, penetrating, abrading and/or contacting surface 17. In an embodiment, the tines may be made of a conductive or non-conductive material and operate to penetrate the skin surface of a patient as described in Fendrock, U.S. Pat. No. 5,305,746, entitled "DISPOSABLE, PRE-GELLED, SELF-PREPPING ELECTRODE," which is incorporated by reference in its entirety herein. In an embodiment, the tines may be a microneedle array, and/or may include channels for conducting a fluid to or from surface 17 (e.g., in drug delivery or fluid sampling contexts). Suitable contact members capable of use with the apparatus and techniques described herein are described in the following disclosures, each of which is incorporated by reference in its entirety herein: Schmidt et al., U.S. Pat. No. 6,785,569, entitled "DRY PHYSIOLOGICAL RECORDING ELECTRODE;" Schmidt et al., U.S. Pat. No. 6,782,283, entitled "DRY PENETRATING RECORDING DEVICE;" Virtanen et al., U.S. Pat. No. 7,366,558, entitled "ELECTRODE FOR OBTAINING A BIOPOTENTIAL SIGNAL;" and Prausnitz et al., U.S. Pat. Publication No. 2005/0137531, entitled "DEVICES AND METHODS FOR ENHANCED MICRONEEDLE PENETRATION OF BIOLOGICAL BARRIERS." It will be understood that any suitable tine configuration may be chosen to suit a context in which a device applicator such as device applicator 10 may be used, with different contexts suggesting appropriate size, shapes, profiles, numbers, lengths, and materials of the tines. A shape change, such as the changes illustrated in FIGS. 1A-1C, may be permanent (which may be advantageous for "single-use" applicators and/or devices) or may be reversible (for applicators and/or devices capable of repeated use). Any of the device applicators described herein may be configured for "single-use" or may be reusable.

Figure 2A:
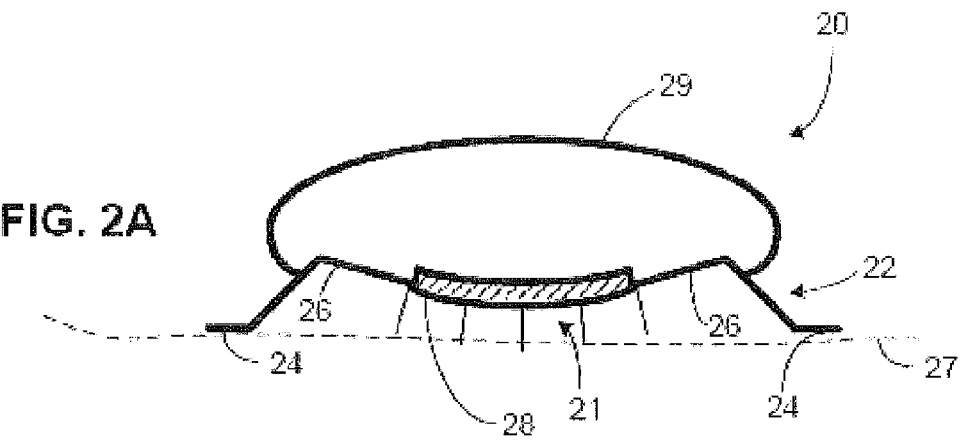
FIGS. 2A-2C depict another illustrative device applicator including a force regulator in accordance with an embodiment.
Figure 2B:
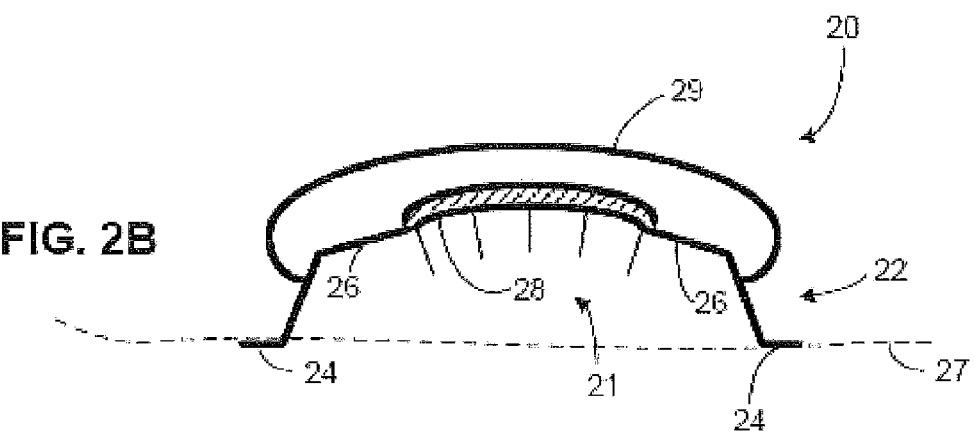
Figure 2C:
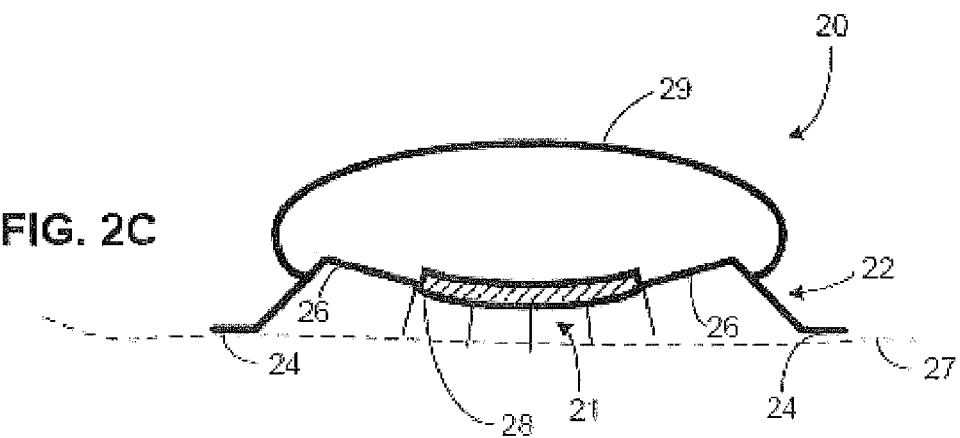

FIGS. 2A-2C depict another illustrative device applicator 20 including force regulator 22 in accordance with an embodiment. As described above with reference to the components of force regulator 12 of FIGS. 1A-1C, force regulator 22 may include supports 24, force directing members 26 and resilient member 28. Device applicator 20 may be configured to interface with device 21, which may have a contact portion. As depicted, a contact portion may include tines. Actuator 29 may also be included with device applicator 20. Broadly, device applicator 20 may drive a contact portion of device 21 toward surface 27 upon release of an applied force (while device applicator 10, as illustrated in FIGS. 1A-1C and described above, may retract a contact portion away from surface 17 upon release of an applied force).

FIG. 2A depicts force regulator 22 in a first, relaxed configuration on surface 27. When downward force is applied to supports 24, force regulator 22 may be deformed into a second, stressed configuration as shown in FIG. 2B. In particular, supports 24 may translate inwardly along surface 27 and force directing members 26 may bow upwardly away from surface 27. Once force directing members 26 have bowed to a predetermined extent, resilient member 28 may move from the downwardly arched position depicted in FIG. 2A to the upwardly arched position depicted in FIG. 2B. The downward force applied to supports 24 may be provided by an operator or mechanical device applying downward pressure to actuator 29, which may be a member capable of translating downward force to supports 24 (such as a rigid dome or plate). In an embodiment, an inwardly-directed lateral force is supplied to supports 24 instead of or in addition to the downward force previously described. Such an inwardly-directed lateral force may result in the same configuration depicted in FIG. 2B, and may be applied by squeezing the sides of force regulator 22 or actuator 29 towards one another. In such an embodiment, actuator 29 may be made from a selectively flexible material or combination of materials (e.g., an elastomeric material) which allows a lateral force to be applied to force regulator 22 by squeezing. When the force is released, resilient member 28 rapidly moves back to its first configuration, and may produce a snapping or clicking sound (FIG. 2C). The other elements of force regulator 22 may also return to their first configurations once the force is released, as depicted in FIG. 2C.

In the embodiments of FIGS. 1A-1C and FIGS. 2A-2C, the transition of the resilient members from the first, relaxed configuration to the second, stressed configuration may occur under predetermined conditions, such as a predetermined force or predetermined extent of bending. These predetermined conditions may be based at least in part on the material or materials comprising the resilient members 18 and 28, respectively, the other elements of the device applicator, and the relative geometry of the components of the device applicator. Similarly, the transition of the resilient members from the second, stressed configuration to the first, relaxed configuration (e.g., the speed of transition, the force of transition) may also depend on these factors. The relationship between these conditions and transitions are in accordance with known principles of materials and mechanics.

As described above, it may be desirable to apply a device to a surface (e.g., a medical device to a patient tissue surface) with a regulated force. This force may desirably be above a threshold force for effective application and/or below a threshold force for effective application, or both. The device applicators described herein allow an operator to apply a device to a surface with an effective amount of force by matching a desired application force with the conditions under which a force regulator member transitions between configurations.

For example, device applicator 10 of FIG. 1A may transition to the second, stressed configuration (FIG. 1B) upon the application of a predetermined magnitude and direction of force applied to force directing members 16. Device applicator 10 is also depicted as including device 11, which comprises a contact portion with tines that may be used to penetrate a patient's stratum corneum in certain medical monitoring and treatment situations. In the first configuration (FIGS. 1A and 1C), the contact portion is spaced away from surface 17. When a predetermined threshold force is provided to force directing members 16, resilient member 18 deflects suddenly and the tines of the contact portion may come in contact with surface 17. This contact may not occur unless a sufficient force is provided, ensuring that the tines of the contact portion contact surface 17 with a force that exceeds a minimum desired amount. Resilient member 18 of FIG. 1A may be configured to prevent an operator from applying too much force.

In some embodiments described herein, a contact portion or device (such as device 11) may include a gel. This gel may have a therapeutic effect (e.g., may contain a medicament or anesthetic) and/or may enhance the efficacy of a treatment applied by device 11. For example, a gel may be a conductive gel used to improve the electrical coupling between surface 17 and an electrode included in device 11; an optical gel used to improve the optical coupling between surface 17 and an optical component (such as an LED or photodiode) included in device 11; or an ultrasound gel used to improve the acoustic coupling between surface 17 and an ultrasound transducer included in device 11. In an embodiment, the gel delivered to or penetrating surface 17 by operation of device applicator 10 may be maintained in its delivered or penetrating state when the contact portion retracts away from surface 17. In other words, the gel may not retract with the tines of the contact portion. In such an embodiment, the gel may continue to provide a benefit, such as maintaining an electrical pathway between device 11 and surface 17, even when the contact portion is retracted or spaced away from surface 17.

Device applicator 20 of FIGS. 2A-2C operates according to a related mechanism. In the first configuration of force regulator 22 (FIGS. 2A and 2C), a contact portion is depicted as being in contact with surface 27. When a predetermined threshold force is provided to force directing members 26, resilient member 28 may deflect suddenly upward and the tines of a contact portion may move away from surface 27. When the force is released, resilient member 28 may return to the first configuration at a predetermined speed dependent upon the mechanical properties of applicator device 20, and thus drive the contact portion towards surface 27 with a predetermined force. Thus, the embodiment illustrated by device applicator 20 ensures that a contact portion is driven into contact with surface 27 with a desired predetermined force, preventing application of device 21 to the surface with too little or too much force.

Additional embodiments of device applicators and force regulating mechanisms are described below. For clarity of illustration, many of the figures and discussion do not explicitly depict a separate actuating member, but an actuator taking any of the forms described herein (e.g., actuators 19 and 29 of FIGS. 1A-1C and FIGS. 2A-2C, respectively) may be used with the force regulation and device application techniques of the present disclosure. It will also be understood that the dimensions of the apparatus depicted in the accompanying figures may be exaggerated for clarity of illustration, and that suitable dimensions may be identified for particular device applicators in accordance with the present disclosure.

FIGS. 3A-3C depict an illustrative force regulator 30 including a bistable spring in accordance with an embodiment. A bistable spring may have two configurations, and transitions between the two configurations may occur by applying an appropriate perturbing force or torque. For example, force regulator 30 is depicted in a first configuration in FIG. 3A. In this configuration, force regulator 30 is longitudinally extended along surface 32, with concave upper face 34 and convex lower face 36. When a sufficient perturbing torque is applied (e.g., by pressing upward in the center of lower face 36 and/or downward at the ends of upper face 34), force regulator 30 may transition to a second configuration, depicted in FIG. 3B. In this second configuration, upper face 34 is convex and lower face 36 is concave relative to surface 32. Applying a downward force to the center of upper face 34 when force regulator 30 is in the second configuration may cause a transition to the first configuration, as depicted in FIG. 3C. As described above with respect to force regulators 10 (FIGS. 1A-1C) and 20 (FIGS. 2A-2C), the transitions between configurations of force regulator 30 may exert predetermined forces on surface 32 (which, as described above, depend upon the geometry and materials of force regulator 30 and known mechanical properties of bistable springs). When a device to be applied to surface 32 is provided on lower face 36 (not shown), the transition from the second configuration (FIG. 3B) to the first configuration (FIG. 3C) will drive the device into contact with surface 32 with the predetermined force.

FIGS. 4A-4C depict illustrative force regulator 40 including a bistable spring in accordance with an embodiment. Force regulator 40 is depicted in a first configuration in FIG. 4A. In this configuration, force regulator 40 is curled longitudinally about its concave upper face 44, with convex lower face 46 facing surface 42. When a sufficient perturbing torque is applied (e.g., by pressing upward in the center of lower face 46 and/or downward at the ends of upper face 44), force regulator 40 may transition to a second configuration, depicted in FIG. 4B. In this second configuration, upper face 44 is convex and lower face 46 is concave relative to surface 42, and force regulator 40 is longitudinally extended along surface 42. Applying a downward force to the center of upper face 44 when force regulator 40 is in the second configuration may cause a rapid transition to the first configuration, as depicted in FIG. 4C. As described above with reference to force regulator 30 (FIGS. 3A-3C), the transitions between configurations of force regulator 40 may exert predetermined forces on surface 42, which may be used to drive a device (not shown) into contact with surface 42.

In some applications, a multi-stage force-regulating mechanism may be desirable. Such a mechanism may include two or more force-regulating components that may operate simultaneously, in sequence, in parallel or in series. The two force-regulating components may have different characteristic time scales (e.g., the time required for a force regulator to transition between configurations) and may regulate an applied force in different ways. It will be understood that the teachings herein regarding device applicators including two-stage force-regulating mechanisms may apply to force-regulating mechanisms with more than two stages. For example, the teachings provided herein may be used to select each of the particular stages of a multiple-stage mechanism, and also may be used to combine these mechanisms to meet a particular applicator design requirement or achieve a particular treatment or therapeutic goal.

FIGS. 5A-5E depict an illustrative device applicator 50 with a two-stage force regulator in accordance with an embodiment. In particular, device applicator 50 may include force regulator 52a and force regulator 52b. Force regulator 52a may operate in a manner similar to force regulator 22 of FIGS. 2A-2C, and may include similarly-oriented components. For example, force regulator 52a may include supports 54a, force directing members 56a and resilient member 58a. Device applicator 50 may be configured to interface with a device, which may have contact portion 55. As depicted, contact portion 55 may include tines. Force regulator 52b may operate in a manner similar to force regulator 12 of FIGS. 1A-1C, and may include similarly-oriented components. For example, force regulator 52b may include supports 54b, force directing members 56b and resilient member 58b. Force regulator 52a may be coupled to force regulator 52b by a rigid connection (for example, by welding or rigid joining), a pivotal connection (e.g., a ball and socket or pin joint), a slightly flexible connection, an adhesive connection, a hook and loop connection, or any suitable mechanical connection.

Figure 5A:
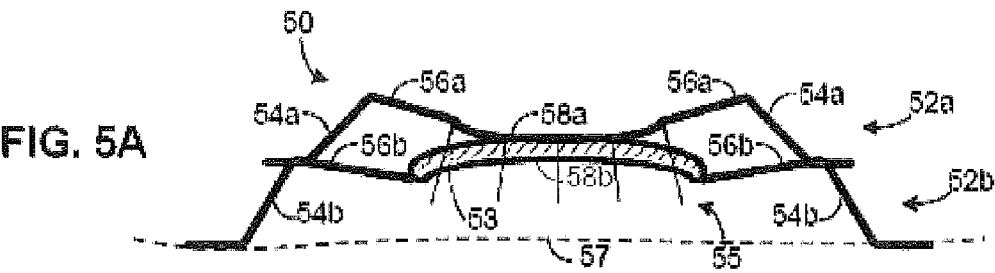
FIGS. 5A-5E depict an illustrative device applicator with a two-stage force regulator in accordance with an embodiment.
Figure 5B:
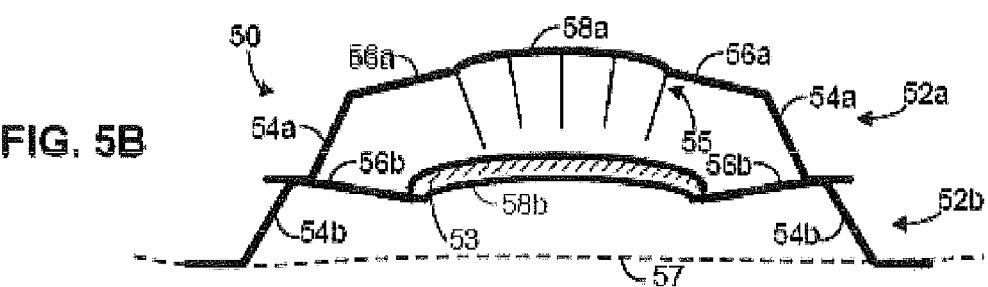

Force regulator 52b may also include an intermediate portion 53. In medical applications, intermediate portion 53 may be a sensing device (such as a passive electrode) or a treatment device (such as an active electrode), as discussed in additional detail below. In the embodiment illustrated in FIGS. 5A-5E, contact portion 55 may be capable of penetrating intermediate portion 53 (e.g., as illustrated in FIGS. 5A, 5D and 5E). Such a mechanism may be enabled in any of a number of ways. For example, intermediate portion 53 may be a porous material, such as a sponge (which may be made from or embedded with conductive filaments if electrical conductivity is desired). In an embodiment, intermediate portion 53 may be a woven or perforated screen, which may be a conductive screen. The interaction of contact portion 55 and intermediate portion 53 is depicted here for illustrative purposes, and such portions may be included with any of the force regulation and device application apparatus described herein. As is also illustrated in the embodiments described herein, force regulation members and contact members may be configured in any of a number of orientations relative to the surface to which a device is to be applied (e.g., adjacent, vertically oriented, opposed, etc.). For example, in an embodiment, a force regulator may be positioned between a contact portion of a device and a surface. In an embodiment, a contact portion of a device may be positioned between a force regulator and a surface.

Force regulators 52a and 52b may act in concert to enable the application and subsequent retraction of contact portion 55 against surface 57. In an embodiment, device applicator 50 may operate as follows. FIG. 5A depicts force regulators 52a and 52b both in first, relaxed configurations on surface 57. When downward force is applied to supports 54a, force regulator 52a may be deformed into a second, stressed configuration as shown in FIG. 5B. In particular, supports 54a may rotate inwardly with respect to surface 57 and force directing members 56a may bow upwardly away from surface 57. Once force directing members 56a have bowed to a pre-determined extent, resilient member 58a may move from the downwardly arched position depicted in FIG. 5A to the upwardly arched position depicted in FIG. 5B. As illustrated in FIG. 5B, the upward arching of resilient member 58a may cause the upward translation (i.e., retraction) of contact portion 55 away from surface 57. As discussed above with reference to FIGS. 2A-2C, a downward force applied to supports 54a may be provided directly by an operator or via an intermediate actuator. In an embodiment, an inwardly-directed lateral force is supplied to supports 54a instead of or in addition to the downward force previously described. Such an inwardly-directed lateral force may result in the same configuration depicted in FIG. 5B, and may be applied by squeezing the sides of force regulator 52a towards one another (e.g., at supports 54a).

Figure 5C:
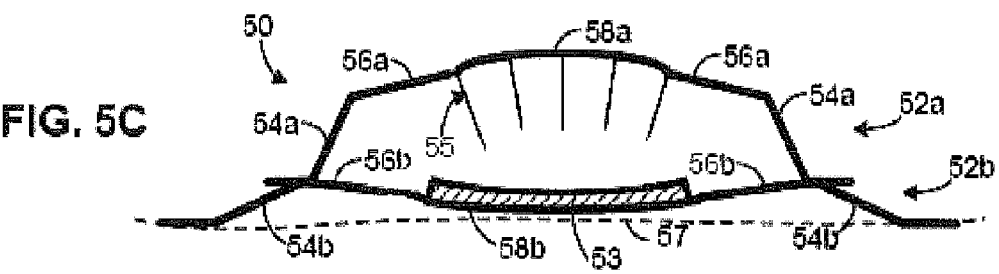
Figure 5D:
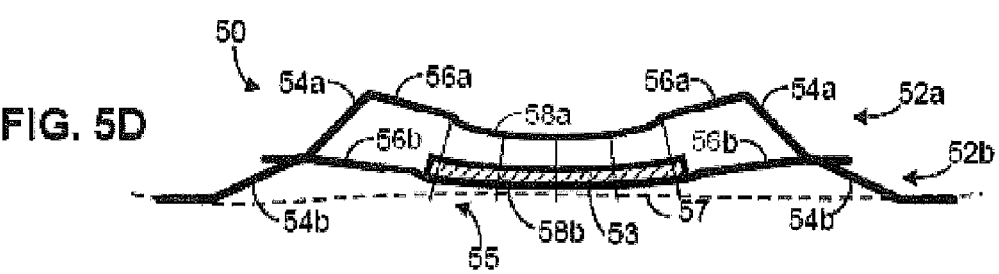
Figure 5E:
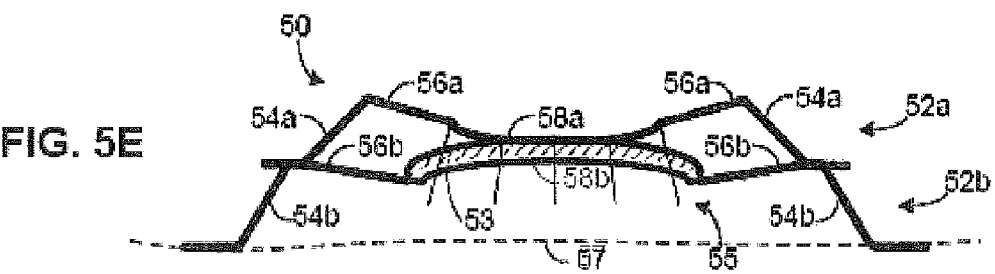

Further, when a downward force is applied to force directing members 56b (e.g., directly by an operator, through an intermediate actuator, or through the coupling with force regulator 52a), force regulator 52b may be deformed into a second, stressed configuration as shown in FIG. 5C. In particular, supports 54b may translate outwardly along surface 57 and force directing members 56b may bow downwardly toward surface 57. Once force directing members 56b have bowed to a predetermined extent, resilient member 58b may move from the upwardly arched position depicted in FIG. 5B to the downwardly arched position depicted in FIG. 5C. As illustrated, the downward arching of resilient member 58b may move intermediate portion 53 closer to surface 57.

When the force provided to supports 54a of force regulator 52a is released, resilient member 58a may move rapidly back to its first configuration, and may produce a snapping or clicking sound, resulting in the configuration of FIG. 59. This transition urges contact portion 55 into contact with surface 57 at a predetermined speed and force related to the mechanical properties of force regulators 52a and 52b. When the force provided to force regulator 52b is released, resilient member 58b may move rapidly back to its first configuration, and may also produce a snapping or clicking sound, as depicted in FIG. 5E. This transition moves contact portion 55 away from surface 57, effectively resulting in a retraction of contact portion 55. Thus, device applicator 50 is one example of an applicator in which contact portion 55 (which may include tines or other contact members) may retract after application to a surface (e.g., a subject patient).

FIGS. 6A-6D depict a second illustrative device applicator 60 with a two-stage force regulator in accordance with an embodiment. Device applicator 60 may include force regulator 62a and force regulator 62b. Force regulator 62a may operate in a manner similar to force regulator 12 (FIGS. 1A-1C), and may include similarly-oriented components. For example, force regulator 62a may include supports 64a, force directing members 66a and resilient member 68a. Device applicator 60 may be configured to interface with a device, which may have contact portion 65. As depicted, contact portion 65 may include tines. Force regulator 62b may initially operate in a manner similar to force regulator 12 (FIGS. 1A-1C), and may include similarly-oriented components. For example, force regulator 62b may include supports 64b, force directing members 66b and resilient member 68b. However, as discussed in further detail below, force regulator 62b may remain in a second configuration after an initial force is applied and released without returning to the first configuration. Force regulator 62a may be coupled to force regulator 62b by a rigid connection (for example, by welding or rigid joining), a pivotal connection (e.g., a ball and socket or pin joint), a slightly flexible connection, an adhesive connection, a hook and loop connection, or any suitable mechanical connection.

Force regulator 62b may also include an intermediate portion 63. In medical applications, intermediate portion 63 may be a sensing device (such as a passive electrode) or a treatment device (such as an active electrode), as discussed above with reference to intermediate portion 53 of device applicator 50 (FIGS. 5A-5E). In the embodiment illustrated in FIGS. 6A-6D, contact portion 65 may be capable of penetrating intermediate portion 63 (e.g., as in FIGS. 6B and 6C). Such a mechanism may be enabled in any of a number of ways as described above with reference to intermediate portion 53 of force regulator 52b.

Figure 6A:
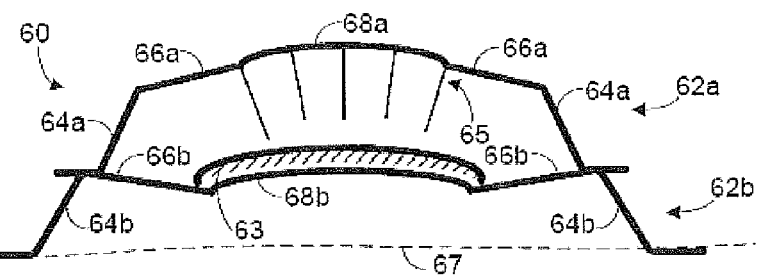
FIGS. 6A-6D depict a second illustrative device applicator with a two-stage force regulator in accordance with an embodiment.
Figure 6B:
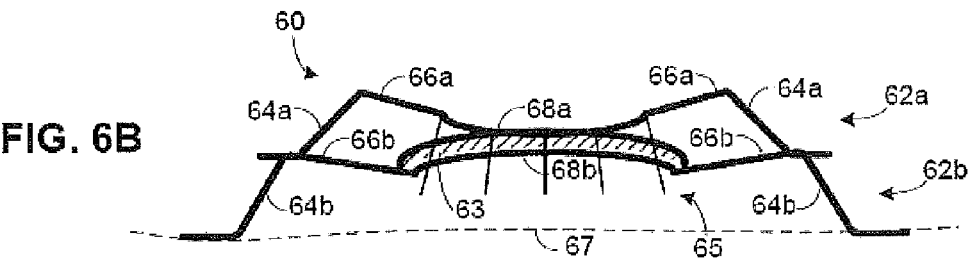

Force regulators 62a and 62b may act in concert to enable the application and subsequent retraction of contact portion 65 against surface 67. In an embodiment, device applicator 60 may operate as follows. FIG. 6A depicts force regulators 62a and 62b both in first, relaxed configurations on surface 67. When a downward force is applied to force directing members 66a, force regulator 62a may be deformed into a second, stressed configuration as shown in FIG. 6B. In particular, supports 64a may translate outwardly and force directing members 66a may bow downwardly toward surface 67. Once force directing members 66a have bowed to a predetermined extent, resilient member 68a may move from the upwardly arched position depicted in FIG. 6A to the downwardly arched position depicted in FIG. 6B. As illustrated, the downward arching of resilient member 68a may move contact portion 65 closer to and/or into contact with surface 67. As discussed above with reference to FIGS. 2A-2C, a downward force applied to force directing members 66a may be provided directly by an operator or via an intermediate actuator. In an embodiment, an outwardly-directed lateral force is supplied to supports 64a instead of or in addition to the downward force previously described. Such an outwardly-directed lateral force may result in the same configuration depicted in FIG. 6B, and may be applied by pulling the sides of force regulator 62a away from one another (e.g., at supports 64a).

Figure 6C:
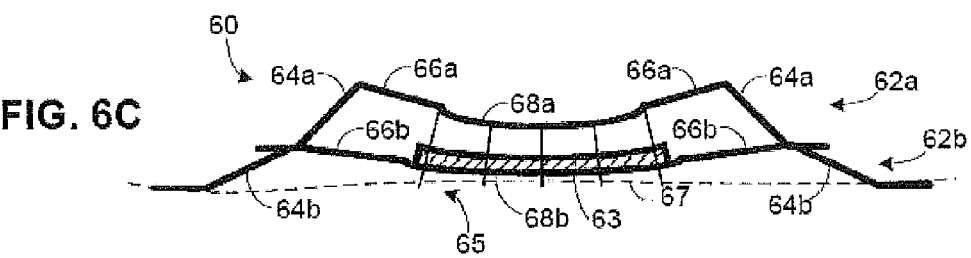
Figure 6D:
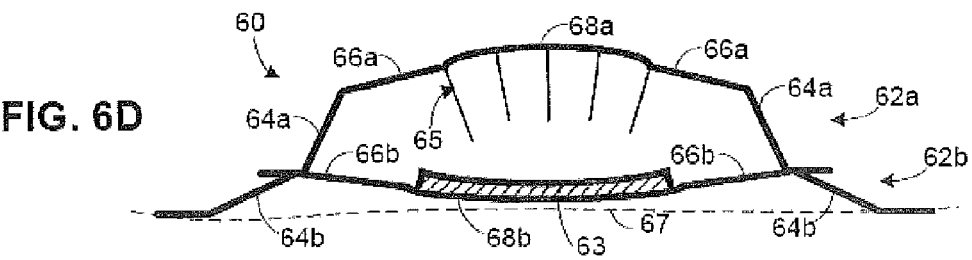

Further, when a downward force is applied to force directing members 66b (e.g., directly by an operator, through an intermediate actuator, or through the coupling with force regulator 62a), force regulator 62b may be deformed into a second, stressed configuration as shown in FIG. 6C. In particular, supports 64b may translate outwardly along surface 67 and force directing members 66b may bow downwardly toward surface 67. Once force directing members 66b have bowed to a predetermined extent, resilient member 68b may move from the upwardly arched position depicted in FIG. 6B to the downwardly arched position depicted in FIG. 6C. As illustrated, the downward arching of resilient member 68b may move intermediate portion 63 closer to surface 67.

When the force provided to supports 64a of force regulator 62a is released, resilient member 68a may move rapidly back to its first configuration, and may produce a snapping or clicking sound, resulting in the structure of FIG. 6I). However, when the force provided to force regulator 62b is released, resilient member 68b may remain in the second configuration due to a permanent deformation of a material comprising force regulator 62b or a mechanical transition (such as a break in force directing members 66b and/or another component). As depicted in FIG. 6I), intermediate portion 63 may remain in close proximity to or in contact with surface 67, while contact portion 65 of force regulator 62a is spaced away from surface 67. Device applicator 60 is one example of an applicator in which contact portion 65 (which may include tines or other contact members) may retract after application to a surface (e.g., a subject patient), but intermediate portion 63 may remain close to or in contact with the surface. In an alternate embodiment utilizing multiple force regulators as described above, a contact portion of a first device regulator (which may include tines) remains in contact with a surface while an intermediate portion is retracted.

Another example of an applicator with a retracting contact portion is illustrated in FIGS. 7A-7E. Device applicator 70 may include force regulator 72a and force regulator 72b. Force regulator 72a may operate in a manner similar to force regulator 22 (FIGS. 2A-2C), and may include similarly-oriented components. For example, force regulator 72a may include supports 74, force directing members 76 and resilient member 78. Device applicator 70 may be configured to interface with a device, which may have contact portion 75. As depicted, contact portion 75 may include tines. Force regulator 72b may be a compressible, resilient member such as a sponge, porous plastic, a highly viscous gel, or an elastomeric material. In an embodiment, force regulator 72b may be saturated with or include a fluid material such as a coupling gel, a drug formulation, or a lubricating fluid. Force regulator 72a may be coupled to force regulator 72b by a rigid connection (for example, by welding or rigid joining), a pivotal connection (e.g., a ball and socket or pin joint), a slightly flexible connection, an adhesive connection, a hook and loop connection, or any suitable mechanical connection.

Force regulator 72b may also include an intermediate portion 73, which may take the form of any of the embodiments described above with reference to intermediate portion 53 of force regulator 52b of FIGS. 5A-5E. In medical applications, intermediate portion 73 may be a sensing device (such as a passive electrode) or a treatment device (such as an active electrode), as discussed in additional detail below. In the embodiment illustrated in FIGS. 7A-7E, contact portion 75 may be capable of penetrating intermediate portion 73 (e.g., as in FIGS. 7A, 7D and 7E). Such a mechanism may be enabled in any of a number of ways, including those discussed above with reference to FIGS. 5A-5E.

Figure 7A:
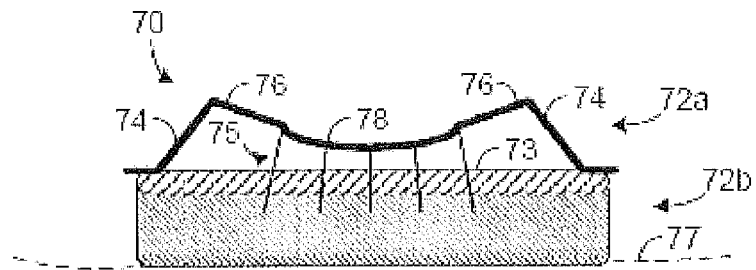
FIGS. 7A-7E depict a third illustrative device applicator with a two-stage force regulator in accordance with an embodiment.

Force regulators 72a and 72b may act in concert to enable the application and subsequent retraction of contact portion 75 against surface 77. In an embodiment, device applicator 70 may operate as follows. FIG. 7A depicts force regulators 72a and 72b both in first, relaxed configurations on surface 77.

Figure 7B:
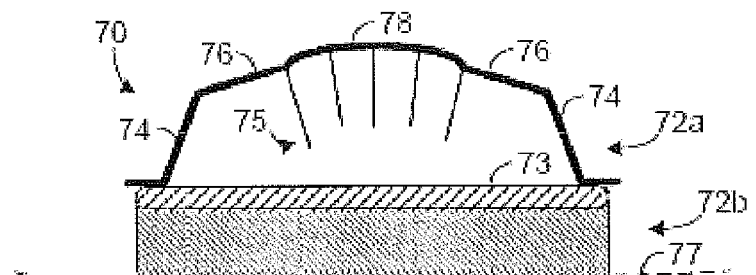

When a suitable force is provided to supports 74 (as discussed with reference to FIGS. 2A-2C), force regulator 72a may be deformed into a second, stressed configuration as shown in FIG. 7B. In particular, supports 74 may rotate inwardly with respect to surface 77 and force directing members 76 may bow upwardly away from surface 77. Once force directing members 76 have bowed to a pre-determined extent, resilient member 78 may move from the downwardly arched position depicted in FIG. 7A to the upwardly arched position depicted in FIG. 7B. As illustrated in FIG. 7B, the upward arching of resilient member 78 may cause the upward translation (i.e., retraction) of contact portion 75 away from surface 77.

Figure 7C:
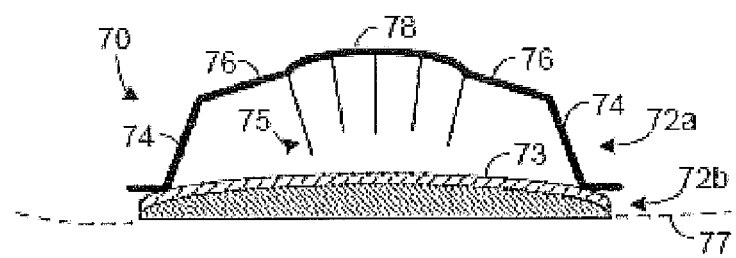

Further, when a downward force is applied to force regulator 72b (e.g., directly by an operator, through an intermediate actuator, or through the coupling with force regulator 72a), force regulator 72b may be deformed into a second, stressed, deformed configuration as shown in FIG. 7C. As illustrated, the compression of force regulator 72b may move intermediate portion 73 closer to surface 77.

Figure 7D:
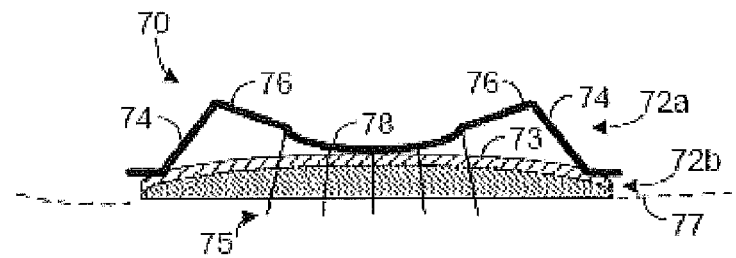
Figure 7E:
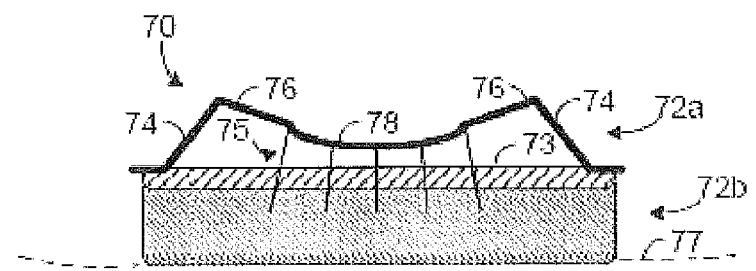

When the force provided to supports 74 of force regulator 72a is released, resilient member 78 may move rapidly back to its first configuration, and may produce a snapping or clicking sound, resulting in the structure of FIG. 7D. This transition urges contact portion 75 into contact with surface 77 at a predetermined speed and force related to the mechanical properties of force regulators 72a and 72b. When the force provided to force regulator 72b is released, force regulator 72b may move back to its first configuration, as depicted in FIG. 7E. This transition moves contact portion 75 away from surface 77, effectively resulting in a retraction of contact portion 75. The depiction of the surface of force regulator 72b as rounded in the second, stressed configuration of FIGS. 7C-7D is merely illustrative; the surface of force regulator 72b may take any shape according to its material composition, geometry and the nature of the applied force.

A fourth example of a device applicator 80 with a retracting contact portion is illustrated in FIGS. 8A-8E. Device applicator 80 may include force regulator 82a and force regulator 82b. Force regulator 82a may operate in a manner similar to force regulator 12 of FIGS. 1A-1C, and may include similarly-oriented components. For example, force regulator 82a may include supports 84, force directing members 86 and resilient member 88. Device applicator 80 may be configured to interface with a device, which may have contact portion 85. As depicted, contact portion 85 may include tines. Force regulator 82b may be a compressible, resilient member such as a sponge, porous plastic, a highly viscous gel, or an elastomeric material, and may include any of the features discussed above with reference to force regulator 72b of device applicator 70. Force regulator 82a may be coupled to force regulator 82b by a rigid connection (for example, by welding or rigid joining), a pivotal connection (e.g., a ball and socket or pin joint), a slightly flexible connection, an adhesive connection, a hook and loop connection, or any suitable mechanical connection.

Figure 8A:
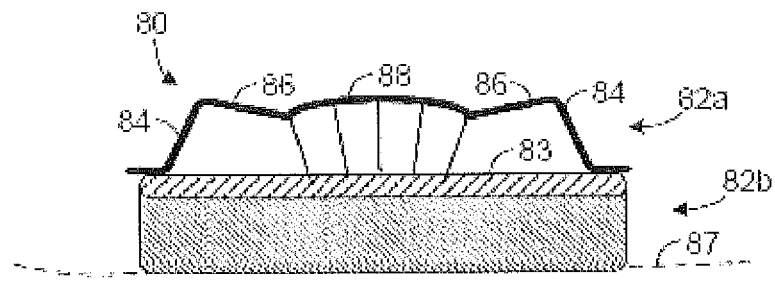
FIGS. 8A-8E depict a fourth illustrative device applicator with a two-stage force regulator in accordance with an embodiment.
Figure 8B:
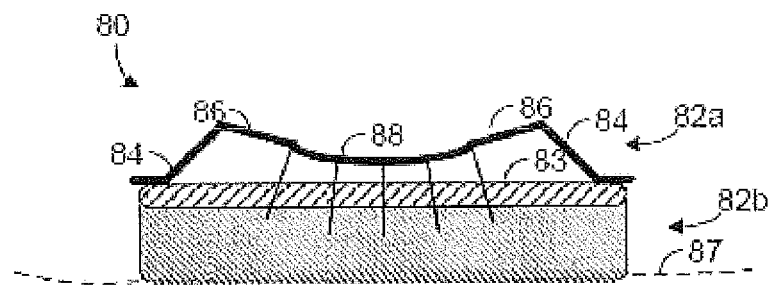

Force regulator 82b may also include an intermediate portion 83, which may include any of the features described above with reference to intermediate portion 53 of device applicator 50 (FIGS. 5A-5E). In the embodiment illustrated in FIGS. 8A-8E, contact portion 85 may be capable of penetrating intermediate portion 83 (e.g., as illustrated in FIGS. 8A, 8D and 8E). Such a mechanism may be enabled in any of a number of ways, including those discussed above with reference to FIGS. 5A-5E.

Force regulators 82a and 82b may act in concert to enable the application and subsequent retraction of contact portion 85 against surface 87. In an embodiment, device applicator 80 may operate as follows. FIG. 8A depicts force regulators 82*a* and 82*b* both in first, relaxed configurations on surface 87. When a suitable force is provided to supports 84 (e.g., as discussed above with reference to FIGS. 1A-1C), force regulator 82*a* may be deformed into a second, stressed configuration as shown in FIG. 8B. In particular, supports 84 may rotate inwardly with respect to surface 87 and force directing members 86 may bow downwardly towards surface 87. Once force directing members 86 have bowed to a pre-determined extent, resilient member 88 may move from the upwardly arched position depicted in FIG. 8A to the downwardly arched position depicted in FIG. 8B. As illustrated in FIG. 8B, the downward arching of resilient member 88 may cause the downward translation of contact portion 85 toward surface 87. The transition of force regulator 82*a* into the second configuration shown in FIG. 8C urges contact portion 85 toward surface 87.

Figure 8C:
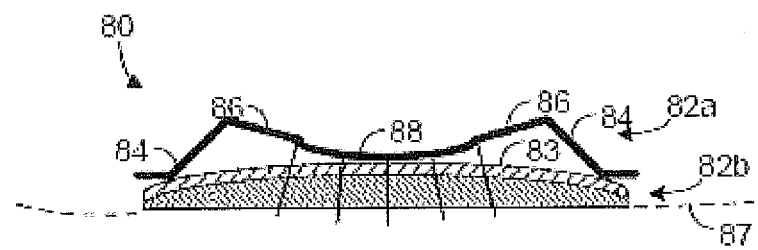
Figure 8D:
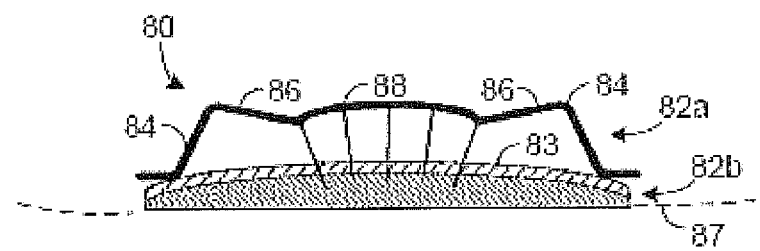
Figure 8E:
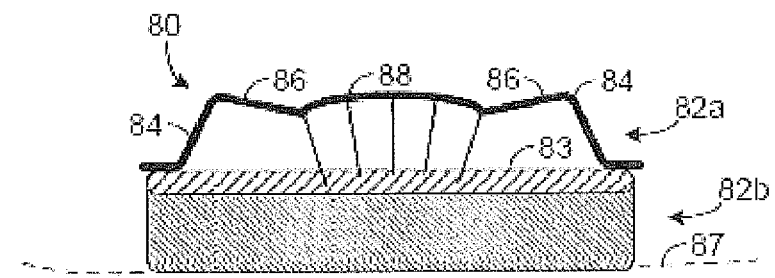

Further, when a downward force is applied to force regulator 82*b* (e.g., directly by an operator, through an intermediate actuator, or through the coupling with force regulator 82*a*), force regulator 82*b* may be deformed into a second, stressed, deformed configuration as shown in FIG. 8C. As illustrated, the compression of force regulator 82*b* may move intermediate portion 83 closer to or into contact with surface 87.

When the force provided to supports 84 of force regulator 82*a* is released, resilient member 88 may move rapidly back to its first configuration, and may produce a snapping or clicking sound, resulting in the structure of FIG. 8D. When the force provided to force regulator 82*b* is released, force regulator 82*b* may move back to its first configuration, as depicted in FIG. 8E. This transition moves contact portion 85 further away from surface 87, resulting in a retraction of contact portion 85. In an alternate embodiment, instead of force regulator 82*b* returning to its first configuration after an applied force is released (as illustrated in FIG. 8E), force regulator 82*b* remains in its second configuration (as illustrated in FIG. 8D). Such an embodiment may be realized, for example, by including a crushable material capable of maintaining a deformation.

The physical dimensions and electrical and mechanical properties of a device applicator may depend on the applicator's intended purpose and environment of use. In an embodiment, a device applicator may be waterproof in order to isolate sensitive or dangerous electrical, chemical and/or mechanical components from fluids in the environment (e.g., conductive fluids used in an electrode application or a patient's bodily fluids). In an embodiment, a device applicator may be sterilizable by heat, chemical and/or irradiation sterilization techniques. In an embodiment, a device applicator may have a low profile to conform more closely to the surface to which it is applied, which may prevent accidental removal of the device and/or the device applicator from a surface.

Described herein are apparatus and techniques for device applicators with contact portions that fully retract (e.g., those in which tines, microneedles and abrading members are spaced away from a surface when the applicator is not actuated), partially retract, or do not retract. Retractable contact portions may be advantageous in environments in which prolonged contact is undesirable. For example, in a medical monitoring/treatment setting, prolonged contact between skin-penetrating tines and a patient's tissue may cause discomfort or irritation. Any of the embodiments described herein may be configured to provide full or partial retraction of a contact portion from a surface, which may allow for longer monitoring/treatment periods, improved signal quality due to decreased patient movement, and better patient and operator compliance. Retractable or partially retractable contact portions may also be advantageous in medical settings in which pressure is continually applied to the device applicator and against a patient's tissue. For example, a patient may be fitted with a forehead electrode sensor during a medical procedure, then positioned face down on an examination table (with his or her face supported by a pillow or protruding through a hole in the examination table). In both of these settings, pressure is continually applied against the device by the table or pillow, driving the device into the patients tissue. By configuring the device applicator to require a threshold force applied to an actuator before the contact portion will engage with a patient's tissue, the discomfort of this continual pressure may be substantially reduced.

When a medical device is to be applied to a patient's tissue, the desired force or force thresholds for application may depend at least in part on a medical protocol to be implemented using the device.

Additionally, a device applicator may be easily actuable when used in a proper manner, and thus may be configured for ease of operation when used as intended. For example, a device applicator that may be used in an easily-accessed location may be actuated by a pushing force perpendicular to a surface to which the device is to be applied. In a location that is more difficult to access (e.g., when a patient attempts to apply a medical device to his or her own back), a device applicator may be actuated by a squeezing mechanism that translates a squeezing force into a force perpendicular to the surface.

Certain of the apparatus and techniques described herein for device application may provide a feedback mechanism to an operator. These feedback mechanisms may be included in a force regulating apparatus, or may be provided as supplemental components. A feedback mechanism may alert an operator when one or more of a number of events has occurred, such as when an appropriate amount of force has been applied and when a force regulator transitions between configurations.

In an embodiment, a feedback mechanism may provide tactile feedback to an operator. Tactile feedback may take the form of any tactile sensation provided to an operator to indicate a state of the device and/or device applicator. For example, an operator providing a force to a device applicator which includes any of the force regulation mechanisms discussed above will experience a sudden change in contact pressure between the operator and the device applicator when the force regulator undergoes certain transitions. For example, an operator pressing down on actuator 19 of device applicator 10 of FIGS. 1A-1C may experience a sudden drop in contact pressure when force regulator 12 transitions from a first configuration (e.g., as illustrated in FIG. 1A) to a second configuration (e.g., as illustrated in FIG. 1B). Subsequently, as an operator releases the downward force from the device applicator when force regulator 12 is in its second configuration (e.g., as illustrated in FIG. 1B), the operator may experience a sudden increase in contact pressure as resilient member 19 moves rapidly upward in its transition back to the first configuration (e.g., as illustrated in FIG. 1C).

Analogously, an operator applying a lateral inward force to supports 24 of device applicator 20 of FIG. 2A may experience a sudden drop in contact pressure as force regulator 22 transitions to a second configuration (e.g., as illustrated in FIG. 2B), and a subsequent increase in contact pressure as force regulator 22 transitions back to the first configuration (e.g., as illustrated in FIG. 2C). Whether an operator experiences an increase, decrease, or other type of change in contact pressure when using any of the device applicators described herein may depend on where and how the operator applies force to the applicator. Consequently, the same device applicator may provide different kinds of tactile feedback (e.g., increases or decreases in pressure) when an operator uses the device applicator in different ways.

In an embodiment, tactile feedback provided to an operator of a device applicator may arise from the breaking or crushing of an element embedded in the device applicator. For example, a device applicator may include a sealed capsule containing air, gel, or another fluid. This capsule may be positioned between the device and the surface to which the device is to be applied, above the device, or in any appropriate location. When an appropriate force is applied to the capsule during operation of the device applicator, the capsule may yield to the force and deform or break. An operator of the device applicator may be able to detect this occurrence tactilely, which may indicate that a sufficient pressure has been applied. In certain embodiments, detecting the breakage of an element of the device applicator may be used as an indicator that too much pressure has been applied, in which case the device may need to be adjusted or a new device and/or applicator should be used.

In an embodiment, a device applicator may include a tactile membrane switch, which are sometimes used in operator-input devices such as keyboards and handheld electronic devices. A tactile membrane switch may be included in any of the device applicators described herein, and may be part of an electronic indicator mechanism as discussed below. Any tactile membrane switch compatible with the techniques described herein may be included in a device applicator in accordance with this disclosure, including those described by Almond et al., U.S. Pat. No. 4,916,275, entitled "TACTILE MEMBRANE SWITCH ASSEMBLY," incorporated by reference in its entirety herein.

In an embodiment, a feedback mechanism may provide auditory feedback to an operator. Auditory feedback may arise from a mechanical or hydrodynamic transition within the device or device applicator, an electrical triggering of an sound source, or a combination of the two. For example, device applicators 10 (FIGS. 1A-1C) and 20 (FIGS. 2A-2C) have previously been described as capable of producing a snapping or clicking sound when their respective force regulators undergo certain transitions between configurations. Such a sound provides auditory feedback to an operator regarding the state of the device and/or device applicator. The bistable spring mechanisms of device applicators 30 (FIGS. 3A-3C) and 40 (FIGS. 4A-4C) may also produce a sound during configuration transitions. Device applicators 50 (FIGS. 5A-5E) and 60 (FIGS. 6A-6D) may produce multiple sounds arising from the multiple mechanical transitions undergone during their operation.

Auditory feedback arising from hydrodynamic effects are also possible. For example, an air bladder or other fluid containing device may be included in any of the embodiments described herein (e.g., embedded in or adjacent to the compressible material of force regulator 62b of FIGS. 6A-6C). When sufficient force is applied, these bladders may release their contents through an aperture, resulting in a squeaking or whistling sound. Auditory feedback may also be generated by electrically-triggered sound sources. These sources may be responsive to an electrical condition within the device or device applicator, such as the deformation of a current-generating piezoelectric material or the closing or opening of a contact switch. Such sources may include a microprocessor or other electronic controller with an output capable of producing sound waves detectable by an operator. Electronic sound sources may be located within the device or device applicator, or may be located remotely (such as in a monitoring or therapy system in communication with the device or device applicator). Additional feedback mechanisms utilizing electronic indicators are described below.

To illustrate a use of the device application techniques described herein, exemplary embodiments of a surface electrode structure capable of use with these techniques will now be described. FIG. 9 is an exploded perspective view of electrode structure 90. In the embodiment of FIG. 9, a flexible circuit may be created by printing a layer of conductive Ag/AgCl ink 92 on flexible substrate 94 (formed from a material such as Mylar or polyester). Other embodiments may utilize carbon, nickel, copper and/or other metal inks.

Basepad 96 (shown with a portion cut away) of 1/16" double-sided adhesive foam with a circular hole of 0.6" diameter, may be placed onto substrate 94 so that the hole is centered concentric to the eyelet. In an embodiment, basepad 96 may include a polyethylene foam. A hole in basepad 96 creates a cylindrical housing which may be used to contain the liquid gel. It will be understood that a hole in basepad 96 may be any suitable shape, such as an ellipse, a polygon, or a shape in conformance with a body region or an electrode.

Electrode 90 may additionally include studded, porous spacer disc 98, which may be approximately 0.6 inches in diameter and made from Velcro hook material. Hooks 99 on disc 98 may be sheared to make tines that may serve as a skin prepping mechanism when a force is applied to disc 98. These tines may prepare the skin in any of the ways described herein (e.g., by piercing or penetrating the stratum corneum). The backing of disc 98 may be porous to allow the gel to go through it and may consequently provides a conductive pathway in the direction perpendicular to the electrode substrate. In an embodiment, the Velcro thickness including the tine profile may be approximately 0.09 inches. The liquid gel may be held in the cylindrical housing by porous spacer sponge 91, which may be made out of a porous material (e.g., a urethane open pore sponge) impregnated with the liquid gel.

Flexible printed trace 93 may electrically connect the electrode to a cable connector (not shown) or to another electrical device. A cable connector may allow the electrode to be connected to a data acquisition system or to a medical therapy delivery unit, such as a pulse oximetry monitor, a continuous non-invasive blood pressure monitor, an EEG monitor, an EKG monitor, a depth of consciousness monitor, a multi-parameter monitor, or any combination thereof.

Certain embodiments may utilize solid hydrogels instead of or in addition to liquid hydrogels. While solid hydrogels have lower conductivities than liquid gels, their use may be advantageous in certain applications. For example, solid hydrogels may be advantageous for sensors which incorporate closely-spaced multiple electrode sensors. In such an application, the higher material crosslinking of the solid hydrogel prevents shorting of the electrode elements due to gel migration, which may occur if liquid gels are used. Such an embodiment may allow the use of solid hydrogels with higher salt content than is commonly used while maintaining a suitably long shelf life.

Certain embodiments may utilize another coupling fluid to improve coupling between a device and a surface to which it is applied. For example, when an applied medical device is an ultrasound transducer, an ultrasound gel may be used to improve the transmission of sound waves between the transducer and a patient's tissue. In an embodiment, a medical device includes one or more optical components (such as electromagnetic emitters and detectors) and a coupling fluid may include an optical coupling material. In an embodiment, a medical device includes one or more mechanical components (such as a massage or vibration transducer) and a coupling fluid may include a lubricating material.

FIGS. 10A-10B depict illustrative device applicators 100*a* and 100*b*, respectively, integrated with the medical device of FIG. 9. Each of device applicators 100*a* and 100*b* may contain components such as basepad 106 and flexible substrate 104 (which may take the form described above for basepad 96 and flexible substrate 94 of FIG. 9, respectively). Device applicator 100*a* of FIG. 10A, as illustrated, may include a force regulator similar to those described above with reference to FIGS. 1A-1C, FIGS. 2A-2C, FIGS. 5A-5E, FIGS. 6A-6D, FIGS. 7A-7E and FIGS. 8A-8E. Device applicator 100*b* of FIG. 10B, as illustrated, may include a force regulator similar to those described above with reference to FIGS. 3A-3C and FIGS. 4A-4C.

As discussed above, certain of the apparatus and techniques described herein for device application may include a feedback mechanism. In an embodiment, a feedback mechanism may include an electronic indicator. FIG. 10A depicts LED 101, which may serve as an illustrative embodiment of such an electronic indicator. Upon applying a device to a surface with an appropriate amount of force, LED 101 may light up as an indicator to an operator. Lit LED 101 may indicate any one or more of a number of conditions to an operator, including when a sufficient force has been applied, when a minimum necessary force has been applied, when a force regulator has undergone a transition, when an event has occurred (e.g., a portion of the applicator device has been bent or loaded to a predetermined degree), when a transformation has occurred (e.g., when a lubricating or conducting gel capsule has burst against the surface), when an electrical condition has occurred (e.g., when a desired electrical connection has been achieved between the surface and the device, or two electrical contacts within the applicator and/or device have closed or opened a circuit), when contact between the device and the surface has been maintained for a sufficient amount of time for successful application, and when contact between the device and the surface has been maintained for a maximum allowable amount of time (i.e., the device should be checked, removed or replaced).

An electronic indicator may be associated with the device itself, or with a device applicator. An electronic indicator may be controlled by a processing device located within the device, within the device applicator, or within a system in electronic communication with the device or device applicator (such as a monitoring or treatment system). In any of the embodiments described herein, electronic communication may occur through wired or wireless transmission.

In an embodiment, an electronic indicator may be powered and/or controlled by a piezoelectric material within the device or device applicator. For example, any of the force regulators or device applicators described herein may include a component made of a piezoelectric material which may be capable of generating current when mechanically deformed. The deformation of a force regulator or related component during device application may cause a piezoelectric component to generate a current which can be used to power or trigger an electronic indicator. A circuit using a power or trigger signal may require a threshold level of current before activating the electronic indicator (e.g., a threshold level of current corresponding to a deformation of a piezoelectric associated with a configuration transition of a force regulator), or may produce an electronic indication that is linearly or non-linearly proportional to the level of current (e.g., an LED growing brighter as the force applied is increased). In an embodiment, a lit LED may extinguish once a sufficient force has been applied to the device, which may also provide an indication to an operator.

Numerous examples of indicators besides LEDs may also be used with the apparatus and techniques disclosed herein. For example, an indicator may be any one or more of an electronically-induced audible tone, a mechanically-induced audible tone (such as a click or a whistle), a display or indication on a monitoring system in electronic communication with an applied device or device applicator, a mechanical vibration, and a temperature change.

In an embodiment, a feedback mechanism may provide another type of visual feedback to an operator, such as one or more of a color change and a shape change. A color change may occur by any of a number of mechanical, chemical and/or electrical mechanisms. In an embodiment, a device or device applicator may include a material or chemical composition that changes color under stress or deformation. Such materials are often used in tamper-evident packaging and labeling. Examples of such materials are provided by Smith et al., U.S. Pat. No. 5,135,262, entitled "METHOD OF MAKING COLOR CHANGE DEVICES ACTIVATABLE BY BENDING AND PRODUCT THEREOF," which is incorporated by reference in its entirety herein.

In an embodiment, a chemical reaction may produce a color change that provides feedback to an operator. Such a chemical reaction may involve the interaction between a previously-contained substance (such as a liquid or gel) and air or another substance (e.g., as occurs in the luminescent reaction underlying glow stick operation), once the container for the previously-contained substance has been broken or opened. A color change may occur when a colored substance previously hidden falls within an operator's view; for example, a colored gel contained in a capsule which releases its contents under pressure and which can subsequently be seen by an operator directly or through a window in a device or device applicator. In medical applications, components and/or products of any such chemical reaction should be non-toxic and bio-compatible, and should not interfere with any medical procedures. In an embodiment, a chemical reaction that provides a color change may also provide a fluid to improve the medical procedure, such as a conductive fluid in an electrical monitoring or treatment procedure.

In an embodiment, a feedback mechanism may include a shape change. For example, an actuator (e.g., actuator 19 of FIG. 1) may deform or collapse once a predetermined pressure is applied, or once a force regulator (e.g., force regulator 12 of FIG. 1) undergoes a configuration transition. A shape change may indicate a successful configuration transition to an operator, such as the shape changes associated with the transitions of force regulator 30 between the configuration of FIG. 3B and the configuration of FIG. 3C. A shape change may be permanent, as illustrated in the embodiment of FIGS. 6A-6D and which may be advantageous for "single-use" applicators and/or devices, or may be reversible (for applicators and/or devices capable of repeated use).

Visual feedback mechanisms may also be used to improve the experience of use of a device applicator for an operator or subject to whom the device is applied. For example, the appearance of the visual feedback mechanism may be pleasing and/or entertaining in pediatric applications to reduce the anxiety of young patients. Further, these visual feedback mechanisms may improve patient compliance with proper use of the device by providing positive reinforcement to a patient when used correctly.

Figure 11A:
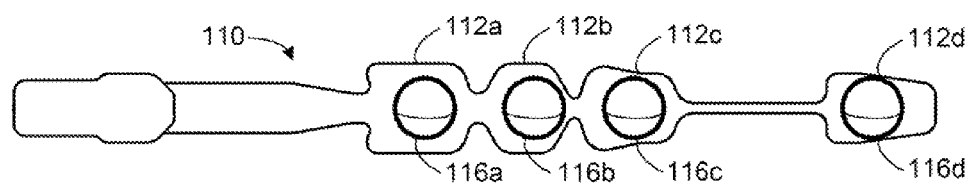
FIGS. 11A and 11B depict top and bottom views, respectively, of an illustrative medical device configured to be applied in accordance with the application techniques described herein.
Figure 11B:
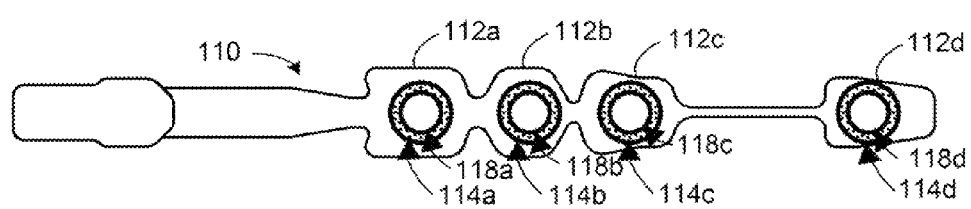

The device application apparatus and techniques described herein may be used with devices that contain one or more contact portions or regions that should come in contact with a surface. For example, FIGS. 11A and 11B depict top and bottom views, respectively, of a illustrative medical device 110 configured to be applied in accordance with the application techniques described herein. Medical device 110 may include regions 112a, 112b, 112c and 112d, each of which includes a contact portion 114a, 114b, 114c and 114d, respectively, that is adapted to contact a subject's tissue (e.g., skin). In FIG. 11A, actuators 116a, 116b, 116c and 116d are illustrated, which may be used to actuate force regulators (not shown) integrated with the medical device in regions 112a, 112b, 112c and 112d, respectively (e.g., as discussed above with reference to FIGS. 9, 10A and 10B). In the embodiment of FIG. 11B, fluid pockets 118a, 118b, 118c and 118d may be included in regions 112a, 112b, 112c and 112d, respectively. A fluid pocket may be a capsule or porous material (e.g., a sponge) containing a gel or other fluid that may be usefully applied at the interface between the subject's tissue and the contact portions. For example, when a medical device includes an electrode or array of electrodes (active or passive), a fluid pocket may contain a conductive gel to improve the coupling between the subject's tissue and the electrodes. A fluid pocket may contain an adhesive fluid to improve adhesion between the subject's tissue and the device. As discussed above, a sealed fluid pocket may burst when the device is applied to the subject's tissue, providing tactile feedback to an operator.

Figure 11C:
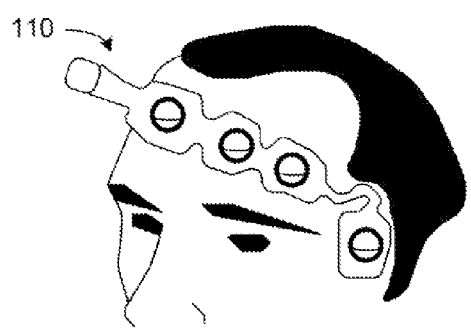
FIG. 11C depicts the illustrative medical device of FIGS. 11A and 11B as applied to a subject's forehead in accordance with an embodiment.

FIG. 11C depicts medical device 110 of FIGS. 11A and 11B as applied to a subject's forehead in accordance with an embodiment. When a flexible underlying substrate is used to integrate regions 112a, 112b, 112c and 112d into device 110, device 110 may be adjustably positioned to conform to a subject's anatomy for successful monitoring and/or treatment. The device applicators of regions 112a, 112b, 112c and 112d may not be identically constructed. In an embodiment, device applicators used with a device may differ in the force provided, the area over which the force is provided, the nature of the application (e.g., applicators with one, two, three or more stages, applicators capable of retracting a contact portion, etc.), and the feedback provided to an operator. The properties of the applicator used with a specific device or device region may depend on a number of factors, including device characteristics, monitoring characteristics, treatment characteristics, subject/surface characteristics and environmental conditions. In an embodiment, the force applied by a device applicator may be based at least in part on a region of the subject to which the device is to be applied (e.g., central forehead, temple, ear, oral cavity, arm, abdomen, heel, over a bony protuberance, over cartilage, internal tissue, physically active area). In an embodiment, the force applied by a device applicator may be based at least in part on the type of subject to which the device is to be applied (e.g., neonate, adult, sensitive skin, wounded tissue, prone patient, supine patient, moving patient).

Figure 12:
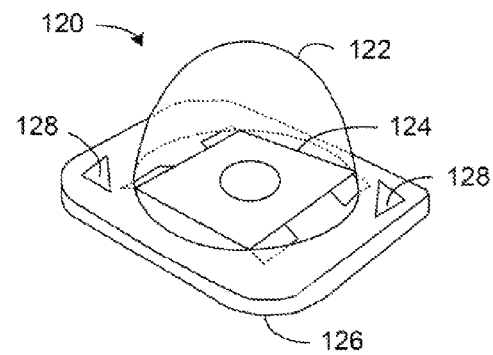
FIG. 12 depicts an illustrative device applicator separate from a device to be applied, in accordance with an embodiment.

As noted above, a device applicator may be integrated with a medical device or may be separate from a medical device. FIG. 12 depicts illustrative device applicator 120 separate from a device to be applied, in accordance with an embodiment. In certain embodiments, a separate device applicator may be single-use (e.g., configured to only apply a single device). In certain embodiments, a separate device applicator may be capable of repeated use with a plurality of separate devices or multiple regions of a single device (as included in device 110 of FIGS. 11A-11B). Device applicator 120 may include many of the elements of any of the device applicators described above, including basepad 126, actuator 122 and force regulator 124. Device applicator 120 may also include registration elements 128, which may allow an operator to align device applicator 120 with a device to be applied and/or with a target region on a surface. In an embodiment, registration elements 128 may be apertures through basepad 126 which allow an operator to view complementary markings on a device and/or surface, or tactilely align registration elements 128 with complementary raised portions of a device and/or surface. Where tactile alignment is desired, registration elements 128 need not be apertures, but may be any protuberance or depression complementary to a protuberance or depression in the surface and/or device to which device applicator 120 is to be aligned. Registration elements 128 may also be electronic components, configured to complete a circuit when properly aligned with a target. Registration elements 128 may be magnetic and in a complementary relationship with magnets disposed in the device and/or surface.

Device applicator 120 may include a component for gripping such as a handle or knob (not shown). Device applicator 120 may be included in a glove or finger cuff, which may improve ease of use, proper application, and may isolate an operator from the surface to which a device is to be applied. Device applicator 120 may include an adhesive on the face of basepad 126 that is intended to contact an application surface, which may help align device applicator 120 to the surface. This adhesive may be a low-tack and/or re-usable adhesive. Device applicator 120 may be provided with one or more associated devices (e.g., in a single box) or may be provided with a cable configured to attach to one or more of the associated devices (e.g., by an elastic cord). In an embodiment, a single device applicator 120 may be flexibly connected to an array of associated devices (e.g., an array similar to those depicted in FIGS. 11A-11C) and may be used to apply one or more of the devices in the array. In a medical environment, such a device applicator may travel with a patient, and may be used by various medical personnel to check and/or reapply one or more of the devices to the patient.

It will be understood that any of the device applicators described above may be used as a preparation device, with or without an associated device to be applied to a patient. For example, any of the device applicators described above may be used to pierce, penetrate, abrade or otherwise prepare a patient's tissue for a medical monitoring and/or treatment procedure, without the inclusion of a medical device. A medical device may be applied after a device applicator has been used to prepare the tissue, or may not be applied. For example, any of the device applicators described above may be used as a preparation device as described in U.S. patent application Ser. No. 13/546,126, filed Jul. 11, 2012, entitled "DEVICE WITH ENCAPSULATED GEL," incorporated by reference in its entirety herein.

The foregoing is merely illustrative of the principles of this disclosure and various modifications can be made by those skilled in the art without departing from the scope and spirit of the disclosure. The following claims may also describe various aspects of this disclosure.

What is claimed is:

1. An apparatus for applying a device to a subject, the apparatus comprising:

a force regulator capable of interfacing with the device, the force regulator capable of first and second configurations, wherein an operator may actuate a transition of the force regulator from the first configuration to the second configuration and wherein the force regulator automatically transitions to the first configuration when in the second configuration;

wherein the force regulator regulates the force with which a contact portion of the device is applied to the subject when the force regulator transitions from the second to the first configuration; and wherein the force regulator moves the contact portion of the device away from the subject when transitioning from the first configuration to the second configuration and towards the subject when automatically transitioning from the second configuration to the first configuration.

2. The apparatus of claim 1, wherein the contact portion is applied to the subject with a predetermined force regulated by the force regulator.

3. The apparatus of claim 2, wherein the predetermined force comprises a maximum amount of force.

4. The apparatus of claim 2, wherein the predetermined force comprises a minimum amount of force.

5. The apparatus of claim 1, further comprising a feedback mechanism to alert the operator when the force regulator transitions to another configuration from at least one of the first and second configurations.

6. The apparatus of claim 5, wherein the feedback mechanism provides tactile feedback to the operator.

7. The apparatus of claim 5, wherein the feedback mechanism provides auditory feedback to the operator.

8. The apparatus of claim 5, wherein the feedback mechanism provides visual feedback to the operator, wherein the visual feedback comprises one or more of a color change and a shape change.

9. The apparatus of claim 5, wherein the feedback mechanism includes an electronic indicator.

10. The apparatus of claim 5, wherein the force regulator comprises the feedback mechanism.

11. The apparatus of claim 1, wherein the force regulator comprises a deformable member.

12. The apparatus of claim 1, wherein the force regulator comprises a leaf spring.

13. The apparatus of claim 1, wherein the force regulator comprises a bistable spring.

14. The apparatus of claim 1, wherein the contact portion of the device comprises tines.

15. The apparatus of claim 14, wherein the tines retract after application to the subject.

16. The apparatus of claim 1, wherein the force regulator is capable of being actuated more than once to apply the contact portion of the device to the subject.

17. The apparatus of claim 1, wherein the force regulator is integral with the medical device.

18. The apparatus of claim 17, wherein the force regulator is positioned above the contact portion of the medical device and the subject.

19. The apparatus of claim 17, wherein the force regulator is positioned between the contact portion of the medical device and the subject.

20. The apparatus of claim 1, wherein the force regulator is separate from the medical device.

21. The apparatus of claim 20, wherein the force regulator is capable of use with a plurality of devices to be applied to a subject.

22. An apparatus for applying a device to a subject, the apparatus comprising:

a first force regulator capable of interfacing with the device, the first force regulator capable of first and second configurations, wherein an operator may actuate a transition of the first force regulator from the first configuration to the second configuration and wherein the first force regulator automatically transitions to the first configuration when in the second configuration; and a second force regulator, positioned between the first force regulator and the subject when the apparatus is applied to the subject and wherein a contact portion of the device interfaced with the first force regulator is capable of penetrating the second force regulator when the first force regulator transitions from the first configuration to the second configuration;

wherein the first and second force regulators regulate the force with which the contact portion of the device is applied to the subject when the first force regulator transitions from the second to the first configuration; and wherein the first force regulator moves the contact portion of the device away from the subject when transitioning from the first configuration to the second configuration and towards the subject when automatically transitioning from the second configuration to the first configuration.

* * * * *